(12) United States Patent
Luo et al.

(10) Patent No.: US 8,686,140 B2
(45) Date of Patent: Apr. 1, 2014

(54) METHOD OF PURIFYING A SALT, SODIUM SALT AND DISODIUM SALT OF PEMETREXED

(75) Inventors: Jie Luo, Chongqing (CN); Meng Lin, Chongqing (CN); Bo Lin, Chongqing (CN); Wenrun Ye, Chongqing (CN); Yongmei Qin, Chongqing (CN); Jie Deng, Chongqing (CN)

(73) Assignee: Chongqing Pharmaceutical Research Institute Co., Ltd. (CN)

( * ) Notice: Subject to any disclaimer, the term of this patent is extended or adjusted under 35 U.S.C. 154(b) by 648 days.

(21) Appl. No.: 12/739,576

(22) PCT Filed: Oct. 21, 2008

(86) PCT No.: PCT/CN2008/072758
§ 371 (c)(1),
(2), (4) Date: Apr. 23, 2010

(87) PCT Pub. No.: WO2009/056029
PCT Pub. Date: May 7, 2009

(65) Prior Publication Data
US 2010/0305319 A1    Dec. 2, 2010

(30) Foreign Application Priority Data

Oct. 24, 2007 (CN) .......................... 2007 1 0092879

(51) Int. Cl.
*C07D 487/04* (2006.01)

(52) U.S. Cl.
USPC .......................................... 544/280

(58) Field of Classification Search
USPC .......................................... 544/280
See application file for complete search history.

(56) References Cited

U.S. PATENT DOCUMENTS

| | | | |
|---|---|---|---|
| 5,254,687 A | 10/1993 | Taylor et al. | |
| 5,625,058 A * | 4/1997 | Pessa et al. | 540/226 |
| 2003/0216416 A1* | 11/2003 | Chelius et al. | 514/265.1 |

FOREIGN PATENT DOCUMENTS

| | | |
|---|---|---|
| CN | 1274362 A | 11/2000 |
| CN | 1406238 A | 3/2003 |
| CN | 1778797 A | 5/2006 |
| CN | 1778802 A | 5/2006 |
| EP | 0432677 A1 | 6/1991 |
| EP | 0549886 A1 | 7/1993 |
| EP | 0589720 A2 | 3/1994 |
| EP | 1018516 | 7/2000 |
| WO | WO 99/16742 A1 | 4/1999 |
| WO | WO 0011004 A1 | 3/2000 |
| WO | WO 01/14379 A2 | 3/2001 |
| WO | WO 01/62760 A2 | 8/2001 |
| WO | WO 2008/021405 A1 | 2/2008 |

OTHER PUBLICATIONS

Mohrig, J. R., Hammond, C. N., Schatz, P. F.,Techniques in Organic Chemistry:Miniscale, Standard Taper Microscale, and Williamson Microscale, 3rd edt, 2010, p. 83.*
Barnett et al., "A Practical Synthesis of Multitargeted Antifolate LY231514", Organic Process Research and Development, no month available, 1999; vol. 3, No. 3, pp. 184-188.
English Abstract of CN 1274362 A, published Nov. 22, 2000, 1 page.
English Abstract of CN 1406238 A, published Mar. 26, 2003, 1 page.
English Abstract of CN 1778797 A, published May 31, 2006, 1 page.
English Abstract of CN 1778802 A, published May 31, 2006, 1 page.
Taylor et al., "A Dideazatetrandrofolate Analogue Lacking a Chiral Center at C-6, N-[4-[2-(2-Amino-3, 4-dihydro-4-oxo-7 H-pyrrolo[2,3-d]pyrimidin-5-yl)ethyl]benzoyl]-L-glutamic Acid, Is aan Inhibitor of Thymidylate Synthase", Journal of Medicine, no month available, 1992, 35, pp. 4450-4454.
"Pemetrexed Disodium", Drugs of Future Use, 1998 23(5), 498-507.
Arakawa et al., "Mechanism of Protein Salting In and Salting Out by Divalent Cation Salts: Balance between Hydration and Salt Binding", Biochemistry, 1984, 23(25), 5912-5923.
Furniss, B.S. et al., "Vogel's Textbook of Practical Organic Chemistry", Fourth Edition, Longman Group Limited, London, 1978, Chapter I,22, 158-162.
Iki et al. "Inclusion Behavior of Thiacalix[4]arenetetrasulfonate toward Water-Miscible Organic Molecules Studied by Salting-Out and X-Ray Crystallography", Organic Letters, Jan. 22, 2002 4(4) 509-512.
Samoilov, "The Theory of Salting out from Aqueous Solutions I. General Problems",Journal of Structural Chemistry, Jan.-Feb. 1966, 7(1) 12-19.

* cited by examiner

*Primary Examiner* — Susanna Moore

(74) *Attorney, Agent, or Firm* — Baker & Hostetler LLP

(57) ABSTRACT

A method of purifying a salt of pemetrexed having a structure of formula (III) by salting-out, wherein if $M_3^+$ is $H^+$, then each of $M_1^+$ and $M_2^+$ is independently $H^+$, $Li^+$, $Na^+$ or $K^+$, provided that both of them are not $H^+$; if $M_3^+$ is $Li^+$, $Na^+$ or $K^+$, then each of $M_1^+$ and $M_2^+$ is independently $Li^+$, $Na^+$ or $K^+$.

III

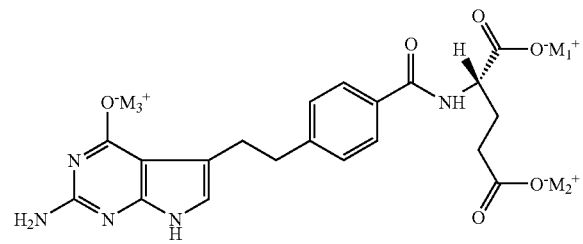

5 Claims, No Drawings

METHOD OF PURIFYING A SALT, SODIUM SALT AND DISODIUM SALT OF PEMETREXED

CROSS-REFERENCE TO RELATED APPLICATIONS

This application is the National Stage of International Application No. PCT/CN2008/072758, filed Oct. 21, 2008, which claims the benefit of Chinese Patent Application No. 200710092879.7, filed Oct. 24, 2007, the disclosures of which are incorporated herein by reference in their entireties.

FIELD OF THE INVENTION

The present invention relates to the fields of organic chemistry and pharmacy. Specifically, the present invention relates to a method of purifying a salt of pemetrexed, sodium salts and disodium salts.

BACKGROUND ART

A salt of pemetrexed are pemetrexed (represented by the structure of formula I) lithium salts, sodium salts and potassium salts and the like, in which sodium salts, i.e., pemetrexed sodium is a sodium salt of pemetrexed, including a monosodium salt, a disodium salt and a trisodium salt, etc. The most common sodium salt is a disodium salt, i.e., pemetrexed disodium, which has a structure of formula II and a chemical name of N-[4-[2-(2-amino-4,7-dihydro-4-oxo-1H-pyrrolo[2,3-d]pyrimidin-5-yl)ethyl]benzoyl]-glutamic acid disodium salt. Various methods for preparing pemetrexed and pemetrexed disodium were disclosed in patents EP432677, EP589720, WO0011004, EP549886 and CN1778797.

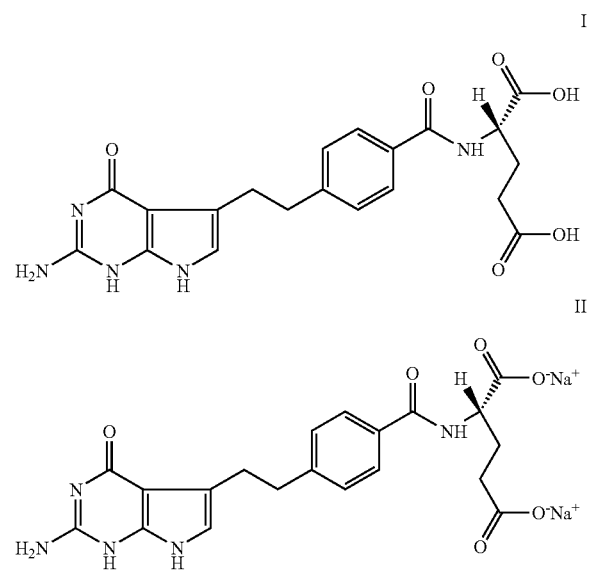

Pemetrexed disodium is a multi-targeted antifolate that strongly inhibits various folate-dependent enzymes, including thymidylate synthase (TS), dihydrofolate reductase (DHFR) and glycinamide ribonucleotide formyltransferase (GARFT). Pemetrexed disodium has been proved effective on a wide variety of solid tumors in clinical trials. At present, pemetrexed disodium is commercial available in USA, the European Union and China etc., which is used for treating malignant pleural stromal tumor as a first-line drug, and local advanced and metastatic non-small cell lung cancer as a second-line drug. In the treatment of malignant pleural stromal tumor, pemetrexed disodium is a unique chemotherapeutic agent in the market currently. In the second-line treatment of non-small cell lung cancer, pemetrexed disodium has a comparative efficacy and reduced toxicities compared with the standard drug Docetaxel, thus, it is hopeful for pemetrexed disodium to become a new standard drug of the second-line treatment for non-small cell lung cancer. In addition, the clinical studies of pemetrexed disodium in the treatment of breast, bowel, pancreatic, head and neck, gastric and bladder cancers are ongoing.

Purification is one of important procedures in the processes for preparing drug materials, and it directly affects the quality of the final products and the cost. At present, all disclosed methods for purifying pemetrexed disodium are crystallization methods using a mixture of an organic solvent and water. WO9916742 and WO0114379 disclose a crystallization method using a mixture of 3A ethanol and water heated to 60-70° C.; Organic Process Research & Development, 1999, 3:184-188, CN1778797 and CN1778802 disclose a crystallization method using a mixture of ethanol and water heated to 45-50° C.; CN1406238 and WO0114379 disclose a crystallization method using a mixture of acetone and water heated to 45-50° C.; furthermore, WO0114379 also discloses a crystallization method using a mixture of isopropanol and water heated to 60-65° C.

In the above methods for purifying pemetrexed disodium, it is generally required to purify pemetrexed prior to the formation of salts at the same time. At present, all disclosed purification methods of pemetrexed are also crystallization methods using a mixture of solvents. J. Med. Chem., 1992, 35:4450-4454 discloses a recrystallization method using a mixture of methanol and acetone; EP432677 discloses a recrystallization method using a mixture of methanol and dichloromethane; CN1406238 discloses a crystallization method using a mixture of 3A ethanol and water heated to 65° C.; Organic Process Research & Development, 1999, 3:184-188 discloses a crystallization method using a mixture of ethanol and water heated to 70-75° C.

Thus, all of the current purification methods of pemetrexed disodium and pemetrexed relate to a crystallization process comprising heating a mixture of solvents. Since pemetrexed disodium and pemetrexed are liable to be oxidized, their oxidation rates will be accelerated under a heating condition, thereby the quality and recovery of the products is reduced. In addition, a mixture of organic solvents is used in the current purification method, thereby the difficulty of recovery or disposal of the solvents and the costs increases greatly.

The present invention made an improvement on the problems existing in the purification methods of pemetrexed disodium in the prior art, such as reduced quality of products under a heating condition and difficulties of recovery and disposal of mixed solvents. It is surprising to find that a salting-out method can be used for purifying pemetrexed disodium effectively. Furthermore, this method can be carried out under a non-heating condition while not using an organic solvent. Accordingly, the present invention provides a method for improving the purification of pemetrexed disodium under a non-heating condition wherein an organic solvent can be avoid using.

SUMMARY OF THE INVENTION

The object of the present invention is to provide an improved method for effectively purifying a salt of pemetrexed, specifically a sodium salt of pemetrexed and more specifically a disodium salt of pemetrexed.

In order to achieve this goal, the present invention provides a method of purifying a salt of pemetrexed having a structure of formula III:

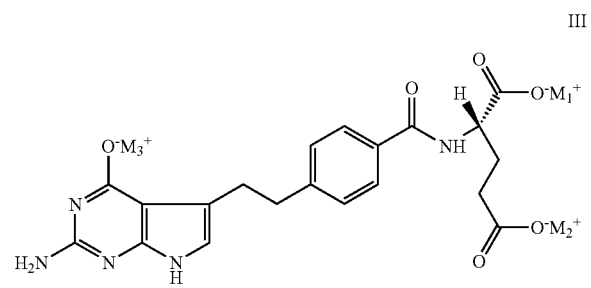

wherein,
if $M_3^+$ is $H^+$, then each of $M_1^+$ and $M_2^+$ is independently $H^+$, $Li^+$, $Na^+$ or $K^+$, provided that both of $M_1^+$ and $M_2^+$ are not $H^+$ (if $M_1^+$, $M_2^+$ or $M_3^+$ is $H^+$, then it represents a hydroxyl together with $O^-$);
if $M_3^+$ is $Li^+$, $Na^+$ or $K^+$, then each of $M_1^+$ and $M_2^+$ is independently $Li^+$, $Na^+$ or $K^+$;
the present method achieves the purification of a salt of pemetrexed by salting-out.

The method comprises crystallizing a salt of pemetrexed from an aqueous solution containing the salt of pemetrexed, one or more other water-soluble salts and optionally one or more water-miscible organic solvents. This method comprises the following steps as shown in Scheme 1.

Scheme I

Step 1. Adding an amount of one or more other water-soluble salts and optionally one or more water-miscible organic solvents to supersaturate a salt of pemetrexed in an aqueous solution;
Step 2. Adjusting the pH of the solution to a value of at least 5 to crystallize the salt of pemetrexed, wherein the adjusting of pH is unnecessary if the pH is already within this range; and
Step 3. Crystallizing sufficiently and then separating the resultant solid by filtration or centrifugation;
to obtain the salt of pemetrexed.

The step 1 of scheme 1 specifically comprises: dissolving a salt of pemetrexed (including dry or wet) or pemetrexed (including dry or wet, converted to salts thereof in advance) in water or a mixed solvents of water and one or more water-miscible organic solvents; then adding an amount of one or more other water-soluble salts as a solid, or an aqueous solution containing an amount of one or more other water-soluble salts and optionally one or more water-miscible organic solvents to form a supersaturated aqueous solution whichfrom a salt of pemetrexed can crystallize sufficiently.

Further, the step 1 of scheme 1 specifically comprises: dissolving a salt of pemetrexed (including dry or wet) or pemetrexed (including dry or wet, converted to salts thereof in advance) in an aqueous solution of one or more other water-soluble salts or a mixed aqueous solution of an amount of one or more other water-soluble salts and one or more water-miscible organic solvents. If a supersaturated aqueous solution that can crystallize sufficiently had already formed in the selected salting-out system, then the step 2 of scheme 1 is carried out after the dissolution; if pemetrexed salt does not precipitate or crystallize sufficiently, then an amount of one or more other water-soluble salts (which can be the same as the salts used for the dissolution or not) as a solid, or an aqueous solution of an amount of one or more other water-soluble salts (which can be the same as the salt used for the dissolution or not), or a mixed solution combined with an aqueous solution of an amount of one or more other water-soluble salts (which can be the same as the salt used for the dissolution or not) and one or more water-miscible organic solvents is added, to form a supersaturated aqueous solution whichfrom a salt of pemetrexed can crystallize sufficiently.

The present invention further provides a method of purifying the sodium salt of pemetrexed (which has a structure of formula III, wherein, If $M_3^+$ is $H^+$, then each of $M_1^+$ and $M_2^+$ is independently $H^+$ or $Na^+$, provided that both of them are not $H^+$; or each of $M_1^+$, $M_2^+$ and $M_3^+$ is independently $Na^+$), the method achieves the purification of the sodium salt of pemetrexed by salting-out. The method comprises salting the sodium salt of pemetrexed from an aqueous solution containing the sodium salt of pemetrexed, one or more other water-soluble sodium salts, and optionally one or more water-miscible organic solvents. This method comprises the following steps as shown in Scheme 2.

Scheme 2

Step 1. adding an amount of one or more other water-soluble sodium salts and optionally one or more water-miscible organic solvents to supersaturate the sodium salt of pemetrexed in the aqueous solution;
Step 2. adjusting the pH of the solution to a value of at least 5 to crystallize the sodium salt of pemetrexed, wherein the adjusting of pH is unnecessary if the pH is already within this range; and
Step 3. crystallizing sufficiently and then separating the resultant solid by filtration or centrifugation;
to obtain the sodium salt of pemetrexed.

The step 1 of scheme 2 specifically comprises: dissolving a sodium salt of pemetrexed (including dry or wet) or pemetrexed (including dry or wet, converted to salts thereof in advance) in water or a mixed solvents combined with water and one or more water-miscible organic solvents; then adding an amount of one or more other water-soluble sodium salts as a solid, or an aqueous solution containing an amount of one or more other water-soluble sodium salts and optionally one or more water-miscible organic solvents to form a supersaturated aqueous solution whichfrom the sodium salt of pemetrexed can crystallize sufficiently.

Further, the step 1 of scheme 2 specifically comprises: dissolving pemetrexed sodium salts (including dry or wet) or pemetrexed (including dry or wet, converted to sodium salts thereof in advance) in an aqueous solution of an amount of one or more other water-soluble sodium salts, or a mixed aqueous solution combined with an aqueous solution of an amount of one or more other water-soluble sodium salts and one or more water-miscible organic solvents. If a supersaturated aqueous solution of the sodium of pemetrexed that can crystallize sufficiently had already formed in the selected salting-out system, then the step 2 of scheme 2 is carried out after the dissolution; if the sodium salt of pemetrexed does not precipitate or crystallize sufficiently, then adding an amount of one or more other water-soluble sodium salts (which can be the same as the sodium salts used for the dissolution or not) as a solid, or an aqueous solution of an amount of one or more other water-soluble sodium salts (which can be the same as the sodium salt used for the dissolution or not), or a mixed solution of an aqueous solution of an amount of one or more other water-soluble sodium salts (which can be the same as the sodium salt used for the dissolution or not) and one or more water-miscible organic solvents is added, to form a supersaturated aqueous solution whichfrom pemetrexed sodium salts can crystallize sufficiently.

Further, the step 1 of scheme 2 specifically comprises: dissolving pemetrexed sodium salts (including dry or wet) or pemetrexed (including dry or wet) converted to sodium salts in an aqueous solution of an amount of one or more other water-soluble sodium salts, or a mixed aqueous solution combined with an aqueous solution of one or more other water-soluble sodium salts and one or more water-miscible organic solvents. If a supersaturated aqueous solution of the sodium salt of pemetrexed that can crystallized sufficiently had already formed in the selected salting-out system, then the step 2 of scheme 2 is carried out after the dissolution; if the sodium salt of pemetrexed does not precipitate or crystallize sufficiently, then adding an amount of one or more other water-soluble sodium salts (which can be the same as the sodium salt used in the dissolution or not) as a solid, or an aqueous solution of an amount of one or more other water-soluble sodium salts (which can be the same as the sodium salt used in the dissolution or not), or a mixed aqueous solution combined with an aqueous solution of one or more other water-soluble sodium salts (which can be the same as the sodium salt used in the dissolution or not) and one or more water-miscible organic solvents, to form a supersaturated aqueous solution whichfrom the sodium salt of pemetrexed can crystallize sufficiently.

The present invention further provides a method of purifying a disodium salt of pemetrexed (which has a structure of formula III, wherein $M_3^+$ is $H^+$, and each of $M_1^+$ and $M_2^+$ is independently $Na^+$) by salting-out. The method comprises salting the disodium salt of pemetrexed out from an aqueous solution containing the disodium salt of pemetrexed, one or more other water-soluble sodium salts and optionally one or more water-miscible organic solvents. This method comprises the following steps as shown in Scheme 3.

Scheme 3

Step 1. Adding an amount of one or more other water-soluble sodium salts and optionally one or more water-miscible organic solvents to supersaturate the disodium salt of pemetrexed in the aqueous solution;

Step 2. Adjusting the pH of the solution to a value of 6-12, preferably 7-9 to crystallize the disodium salt of pemetrexed, wherein the adjusting of pH is unnecessary if the pH is already within this range; and Step 3. Crystallizing sufficiently and then separating the resultant solid by filtration or centrifugationm;

to obtain the disodium salt of pemetrexed.

The step 1 of scheme 3 specifically comprises: dissolving a sodium salt of pemetrexed (including dry or wet) or pemetrexed (including dry or wet, converted to sodium salts thereof in advance) in water or a mixed solvent combined with water and one or more water-miscible organic solvents; then adding an amount of one or more other water-soluble sodium salts as a solid, or an aqueous solution of an amount of one or more other water-soluble sodium salts, or a mixed aqueous solution combined with an aqueous solution of an amount of one or more other water-soluble sodium salts and one or more water-miscible organic solvents, to form a supersaturated aqueous solution whichfrom the disodium salt of pemetrexed can crystallize sufficiently.

Further, the step 1 of scheme 3 specifically comprises: dissolving a sodium salt of pemetrexed (including dry or wet) or pemetrexed (including dry or wet, converted to sodium salts thereof in advance) in an aqueous solution of an amount of one or more other water-soluble sodium salts, or a mixed aqueous solution combined with an aqueous solution of an amount of one or more other water-soluble sodium salts and one or more water-miscible organic solvents. If a supersaturated aqueous solution of the disodium salt of pemetrexed that can crystallize sufficiently had already formed in the selected salting-out system, then the step 2 of scheme 3 is carried out after the dissolution; if the disodium salt of pemetrexed does not precipitate or crystallize sufficiently, then adding an amount of one or more other water-soluble sodium salts (which can be the same as the sodium salt used for the dissolution or not) as a solid, or an aqueous solution of an amount of one or more other water-soluble sodium salts (which can be the same as the sodium salt used for the dissolution or not), or a mixed aqueous solution combined with an aqueous solution of an amount of one or more other water-soluble sodium salts (which can be the same as the sodium salt used for the dissolution or not) and one or more water-miscible organic solvents, to form a supersaturated aqueous solution whichfrom the disodium salt of pemetrexed can crystallize sufficiently.

A preferred method for purifying pemetrexed disodium by salting-out comprises salting the disodium salt of pemetrexed out from an aqueous solution containing the disodium salt of pemetrexed and one other water-soluble salt. This method comprises the following steps as shown in Scheme 4.

Scheme 4

Step 1. Adding an amount of one or more other water-soluble sodium salts to supersaturate the disodium salt of pemetrexed in the aqueous solution;

Step 2. Adjusting the pH of the solution to a value of 6-12, preferably 7-9 to salting the disodium salt of pemetrexed out, wherein the adjusting of pH is unnecessary if the pH is already within this range; and Step 3. Crystallizing sufficiently and then separating the resultant solid by filtration or centrifugation;

to obtain the disodium salt of pemetrexed.

The step 1 of scheme 4 specifically comprises: dissolving a sodium salt of pemetrexed (including dry or wet) or pemetrexed (including dry or wet, converted to sodium salts thereof in advance) in water; then adding an amount of other water-soluble sodium salt as a solid, or an aqueous solution of an amount of other water-soluble sodium salt, to form a supersaturated aqueous solution whichfrom the disodium salt of pemetrexed can crystallize sufficiently.

Further, the step 1 of scheme 4 specifically comprises: dissolving a sodium salt of pemetrexed (including dry or wet) or pemetrexed (including dry or wet, converted to sodium salts thereof in advance) in an aqueous solution of an amount of other water-soluble sodium salts. If a supersaturated aqueous solution of the disodium salt of pemetrexed that can crystallize sufficiently had already formed in the selected salting-out system, then the step 2 of scheme 4 is carried out after the dissolution; if the disodium salt of pemetrexed does not precipitate or crystallize sufficiently, then adding an amount of the same water-soluble sodium salt as a solid, or an aqueous solution of an amount of the same water-soluble sodium salt, to form a supersaturated aqueous solution whichfrom the disodium salt of pemetrexed can crystallize sufficiently.

Each compound having the structures of I-III can be present in the form of the equilibrium mixture of tautomers thereof. The following partial structures represent the parts of the structures tautomerizing in the molecule,

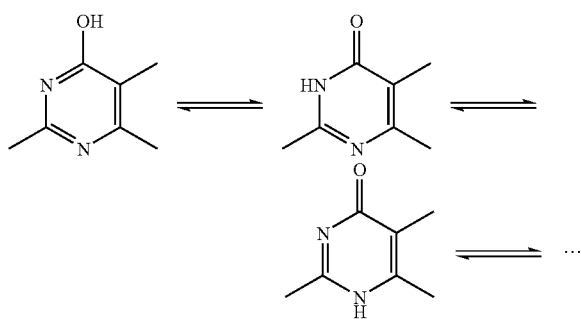

For the convenience of description, only tautomeric 4(1H)-oxo form and its related name are discussed in the specification. It should be understood that such description comprises the corresponding tautomeric 4-hydroxyl and 4(3H)-oxo form, etc.

"A salt of pemetrexed" as used herein comprises a monosalt, a disalt and a trisalt of pemetrexed, or a mixture thereof. Pemetrexed has two hydrogen atoms in carboxyl groups and one hydrogen atom in the hydroxyl group (which can tautomerized into a carbonyl group) of the pyrimidine ring, thereby these hydrogen atoms exhibit acidic, and salts can be formed. For the acidity, the acidity of two hydrogen atoms in the carboxyl groups is comparable, which is stronger than that of the hydrogen atom in the hydroxyl group of the pyrimidine ring, therefore, a disalt of pemetrexed formed with the two carboxyl groups are the most common forms among a salt of pemetrexed. "A sodium salt of pemetrexed" as used herein comprises a monosodium salt, a disodium salt and a trisodium salt of pemetrexed, or a mixture thereof, in which a disodium salt of pemetrexed formed with the two carboxyl groups are the most common form among the sodium salts of pemetrexed.

"Salting-out" as used herein refers to the process that one salt precipitates from a solution under the effect of one or more other salts.

"Water-soluble salts" as used herein refer to organic or inorganic lithium salts, sodium salts or potassium salts having a certain solubility in water which are weak acidic, neutral or basic. "Water-soluble sodium salts" refer to organic or inorganic sodium salts having a certain solubility in water which are weak acidic, neutral or basic. Water-soluble inorganic sodium salts include but not limited to sodium fluoride, sodium chloride, sodium bromide, sodium iodide, sodium hydroxide, sodium sulfide, sodium carbonate, sodium bicarbonate, sodium nitrate, sodium nitrite, sodium phosphate, sodium dihydrogen phosphite, disodium hydrogen phosphite, sodium hypophosphorate, sodium pyrophosphate, sodium hydrogen pyrophosphate, sodium sulfate, sodium sulfite, sodium hyposulfite, sodium pyrosulfate, sodium pyrosulfite, sodium bisulfite, sodium thiosulphate, sodium borate and sodium molibdate, etc. Water-soluble organic sodium salts include but not limited to sodium fatty carboxylates, such as sodium formate, sodium acetate, sodium propionate, sodium isovalerate, sodium oxalate, sodium citrate, sodium citrate, sodium glutamate, sodium tartrate, disodium edetate, etc.; sodium aromatic carboxylates, such as sodium benzoate, sodium salicylate, sodium nitrobenzoate, sodium benzene dicarboxylate, etc.; sodium sulfonates, such as sodium methanesulfonate, sodium methanesulfonate dihydrate, sodium ethanesulfonate, sodium benzenesulfonate, sodium p-toluenesulfonate, etc.; phenol sodium salts, such as sodium phenolate, disodium diphenolate, sodium nitrophenolate, etc.; other sodium salts, such as sodium saccharin etc. Among them, the sodium salts with stronger alkalinity are generally used with other neutral sodium salts or those with weak alkalinity. In addition to the salting-out effect, they are also used to adjust the pH of the system. Among these water-soluble sodium salts, sodium chloride, sodium bromide, sodium iodide, sodium sulfate, sodium formate, sodium acetate and sodium methanesulfonate are preferred. Sodium chloride, sodium formate and sodium acetate are more preferred. Water-soluble lithium salts or potassium salts can be selected from the corresponding lithium salts or potassium salts of acid groups of the above sodium salts.

The expression "one other" in "one or more other water-soluble salts" means that only one water-soluble lithium salt, sodium salt or potassium salt which acid part is not pemetrexed is used in the salting-out operation for the purpose of salting-out. The salting-out system perhaps contains a small amount of other water-soluble salts incorporated for other purposes, for example, when hydrochloric acid or sodium hydroxide solution is used to adjust the pH, a small amount of sodium chloride or sodium hydroxide would be incorporated into the salting-out system. The expression "more other" means that two or more water-soluble lithium salt, sodium salt or potassium salt which acid part is not pemetrexed is used in the salting-out operation for the purpose of salting-out. Likewise, the expression "one other" in "one or more other water-soluble sodium salts" means that only one water-soluble sodium salt which acid part is not pemetrexed is used in the salting-out operation for the purpose of salting-out. The salting-out system perhaps contains a small amount of other water-soluble sodium salts incorporated for other purposes. The expression "more other" means that two or more water-soluble sodium salts which acid part is not pemetrexed are used in the salting-out operation for the purpose of salting-out.

"Water-miscible organic solvents" as used herein include but not limited to ethanol, methanol, isopropanol, acetone, tetrahydrofuran, acetonitrile, glycol dimethyl ether, N,N-dimethylformamide, N,N-dimethylacetamide, dimethyl sulfoxide, etc. They can be used to adjust the solubility of each salt in the salting-out system, so as to increase the amount of precipitated salt of pemetrexed (or a sodium salt or disodium salt of pemetrexed). The amount of the solvents will be suitable to allow the other salts which acid parts are not pemetrexed in the salting-out system not precipitate markedly.

The aim of "adding water-soluble salts (or sodium salts) (including a solid or solution thereof)" in step 1 of Schemes 1-4 is to increase the concentration of salts (or sodium salts) for salting-out used in the salting-out system, thereby reduce the solubility of a salt of pemetrexed (or a sodium salt of pemetrexed or a disodium salt of pemetrexed) in the salting-out system to form a supersaturated solution and precipitate. "An amount of" means that the total amount of "water-soluble salts (or sodium salts)" added is suitable to allow a salt of pemetrexed precipitate well and other salts not precipitate markedly. The concentration of "water-soluble salts (or sodium salts)" added for the purpose of well crystallization is usually not lower than that of "water-soluble salts (or sodium salts)" added for the purpose of dissolving a salt of pemetrexed (or a sodium salt of pemetrexed), preferably from half saturated concentration to saturated concentration. For steps 1-2, the total amount of water in the salting-out system is usually between 4 and 80 folds, preferably between 10 and 40 folds, based on the weight of a dry salt of pemetrexed (or a dry sodium salt of pemetrexed or a dry disodium salt of pemetrexed). If a wet salt of pemetrexed (or a wet sodium salt of pemetrexed or a wet disodium salt of pemetrexed) is used, they should be converted to the weight of a dry salt of pemetrexed (or a dry sodium salt of pemetrexed or a dry disodium salt of pemetrexed). The total molarity of water-soluble salts (or sodium salts) for salting-out is usually between 0.1 fold and saturated concentration, preferably between 20% saturated concentration and saturated concentration, based on the molarity of a salt of pemetrexed (or a sodium salt of pemetrexed).

"Half saturated concentration" and "20% saturated concentration" mentioned above mean the concentration when the dissolved amount of one or more salts is half and 20% of the saturated dissolved amount under such condition respectively.

"To supersaturate" in step 1 of Schemes 1-4 is relative to the desired target a salt of pemetrexed (or a sodium salt of pemetrexed or a disodium salt of pemetrexed), but the aqueous solution in step 1 does not always contain these target salts, that is to say, with regard to non-target a salt of pemetrexed, the aqueous solution in step 1 may be saturated or unsaturated, whereas, if these non-target salts are converted to target salts (for example, by adjusting pH), such target salts are supersaturated in the aqueous solution. For example, adding an amount of other water-soluble sodium salt to a strong basic aqueous solution containing a sodium salt of pemetrexed, adjusting the pH and then salting the disodium salt of pemetrexed out. In the present invention, the aqueous solution prior to the pH adjustment is considered as "supersaturate the disodium salt of pemetrexed in an aqueous solution", whereas, the aqueous solution prior to the pH adjustment is not always supersaturated with respect to the sodium salt of pemetrexed which may be a trisodium salt, etc.

For the operation procedures in step 1 of Scheme 1, "converting pemetrexed to a salt thereof" is achieved by reaction with a basic reagent containing lithium, sodium or potassium. For the operation procedures in step 1 of Schemes 2-4, "converting pemetrexed to a sodium salt thereof" is achieved by reaction with a basic reagent containing sodium. These basic reagents containing sodium include but not limited to sodium hydroxide, sodium carbonate, sodium phosphate, sodium formate, sodium acetate, etc., in which sodium hydroxide, sodium formate and sodium acetate are preferred.

For the operation procedures in step 1 of Schemes 1-4, if a salt of pemetrexed (or pemetrexed sodium salts) can not dissolve well, or pemetrexed can not be converted to salts (or sodium salts) thereof to achieve dissolution, the pH of the system can be raised using a base to promote dissolution, the pH is usually not lower than that to be achieved after the adjustment in step 2. In general, the pH is higher than that to be achieved after the adjustment in step 2 by 0-6 units, preferably 1-4 units. If the pH of the solution in step 1 is lower than that to be achieved after the adjustment in step 2, then in step 1, the pH is usually adjusted to a value that is not lower than that to be achieved after the adjustment in step 2, the pH is usually adjusted to a value that is higher than that to be achieved after the adjustment in step 2 by 0-6 units, preferably 1-4 units. If it is inconvenient to adjust the pH in step 2 (for example, the system crystallizes rapidly and becomes slurry), the pH can be pre-adjusted in step 1 in order to meet the pH requirement for crystallization.

For the operation procedures in steps 1-2 of Scheme 1, "the pH of the system" is adjusted with an acid or a base containing lithium, sodium or potassium. For the operation procedures in steps 1-2 of Schemes 2-4, "the pH of the system" is adjusted with an acid or a base containing sodium. "A base containing sodium" include but not limited to sodium hydroxide, sodium carbonate, sodium bicarbonate, sodium phosphate, disodium hydrogen phosphate, sodium formate, sodium acetate, sodium oxalate, sodium benzonate, etc., in which sodium hydroxide, sodium carbonate, sodium formate and sodium acetate are preferred. "An acid" include but not limited to hydrochloric acid, hydrobromic acid, hydroiodic acid, sulphuric acid, phosphoric acid, nitric acid, sodium bisulphate, sodium dihydrogen phosphate, formic acid, acetic acid, oxalic acid, trifluoroacetic acid, methanesulfonic acid, p-toluenesulfonic acid, benzonic acid, etc., in which hydrochloric acid, hydrobromic acid, sulphuric acid, formic acid and acetic acid are preferred.

For the operation procedures in step 2 of Schemes 1-4, sometimes, an amount of water, one or more water-soluble salts (or sodium salts), one or more water-miscible organic solvents or a mixture thereof can be supplemented, in order to improve the fluidity of the system or further increase the recovery of salts by salting-out.

For the operation procedures in steps 1 and 3 of Schemes 1-4, "crystallize sufficiently" means that no more a salt of pemetrexed (or a sodium salt of pemetrexed or a disodium salt of pemetrexed) essentially crystallize before other salts crystallize evidently, or a salt of pemetrexed (or a sodium salt of pemetrexed or a disodium salt of pemetrexed) have crystallized just before other salts are to crystallize evidently.

For the steps 1-3 of Schemes 1-4, the range of the operation temperature is wide. In general, the temperature is 0-80° C., preferably 10-40° C.

The operation procedures of Schemes 1-4 are essentially the same, and the main difference is that the resulting object and the corresponding salting-out agent are different, thus, for the sake of concision, "( )" in the above description indicates that different embodiments are suitable for different subjects. For example, "a salt of pemetrexed (or a sodium salt of pemetrexed or a disodium salt of pemetrexed)" indicates that such an expression refers to "a salt of pemetrexed" in Scheme 1, or the corresponding "a sodium salt of pemetrexed" in Scheme 2, or the corresponding "a disodium salt of pemetrexed" in Schemes 3 and 4; also, "water-soluble salts (or sodium salts) indicates that such an expression refers to "water-soluble salts" in Scheme 1, or the corresponding "water-soluble sodium salts" in Schemes 2-4; furthermore, "a salt of pemetrexed (or a sodium salt of pemetrexed)" indicates that such an expression refers to "a salt of pemetrexed" in Scheme 1, or the corresponding "a sodium salt of pemetrexed" in Schemes 2-4.

Since the impurities in crude a salt of pemetrexed (or a sodium salt of pemetrexed or a disodium salt of pemetrexed) or crude pemetrexed are essentially water-soluble, the precipitation of a salt of pemetrexed (or a sodium salt of pemetrexed or a disodium salt of pemetrexed) from the aqueous solution can effectively reduce or remove these impurities, thereby enhance greatly the purities of products. The crude disodium salt of pemetrexed or crude pemetrexed of various purities were purified by the above operation procedures and satisfactory refine results were obtained. In general, pharmaceutical grade products can be obtained by performing this salting-out operation once or twice.

A lithium salt or a potassium salt of pemetrexed can also be purified using the above methods.

In conclusion, the present invention provides a new method of purifying a salt of pemetrexed, specifically a sodium salt of pemetrexed and more specifically a disodium salt of pemetrexed by salting-out. This method differs from the crystallization method using mixed solvents in the prior art in that the principle of salting-out is applied in this method. In addition, this method can be carried out at ambient temperature without organic solvents, thereby avoid the disadvantages including reduced quality of products under a heating condition and difficulties of recovery of mixed solvents in the prior art. Furthermore, such a method is easy to operate and exhibits superior refinement effect, and thus is convenient to industrialization.

DETAILED DESCRIPTION OF THE INVENTION

The present invention is further illustrated in combination with the following examples. These examples are provided to exemplify the present invention, but are not intended to restrict the scope of the present invention in any way. The terms and abbreviations in the examples have their common meanings. For example, "° C.", "HPLC" and "g" represent "Celsius degree", "high performance liquid chromatography" and "gram" respectively.

EXAMPLE 1

Purification of Disodium Pemetrexed 10.0 g of crude disodium pemetrexed (the purity is 97.7%, as measured by HPLC) was added to 100 g of 25% saturated sodium chloride aqueous solution at 20-30° C., then the resulting mixture was adjusted to pH 11-12 using sodium hydroxide solution to obtain a clear solution. 100 g of half saturated sodium chloride aqueous solution was added with stirring, then the resulting mixture was adjusted to pH 8 using hydrochloric acid solution. The mixture was stirred additional 1-2 h at 20-30° C. and filtrated. The cake was washed with an appropriate amount of aqueous ethanol and dried to obtain 8.8 g of disodium pemetrexed. The purity of the resulting disodium pemetrexed is 99.7% as measured by HPLC.

EXAMPLE 2

Purification of Disodium Pemetrexed 10.0 g of crude disodium pemetrexed (the purity is 97.7%, as measured by HPLC) was dissolved in 150 g of water at 20-30° C., and 15.0 g of sodium chloride was added with stirring, then the resulting mixture was adjusted to about pH 8 using a sodium hydroxide solution. The mixture was stirred additional 1-2 h at 20-30° C. and filtrated. The cake was washed with an appropriate amount of aqueous ethanol and dried to obtain 8.6 g of disodium pemetrexed. The purity of the resulting disodium pemetrexed is 99.6% as measured by HPLC.

EXAMPLE 3

Purification of Disodium Pemetrexed 61 g of crude, wet pemetrexed (the purity is 88.5%, as measured by HPLC) (corresponding to about 20 g of dry pemetrexed) was added to an aqueous sodium formate solution formed with 70 g of water and 10 g of sodium formate under a nitrogen atmosphere at ambient temperature, then the resulting mixture was adjusted to about pH 8 using sodium hydroxide or hydrochloric acid solution to dissolve the added pemetrexed. Then an aqueous sodium formate solution formed with 140 g of water and 30 g of sodium formate was added. The mixture was stirred additional 1-2 h at ambient temperature and filtrated. The cake was washed with an appropriate amount of aqueous ethanol and dried to obtain 18.6 g of disodium pemetrexed. The purity of the resulting disodium pemetrexed is 99.2% as measured by HPLC.

If the above purification procedure was repeated once more, the purity of the resulting disodium pemetrexed is 99.8%.

EXAMPLE 4

Purification of Disodium Pemetrexed 61 g of crude, wet pemetrexed (the purity is 88.5%, as measured by HPLC) (corresponding to about 20 g of dry pemetrexed) was added to an aqueous sodium formate solution formed with 70 g of water and 10 g of sodium formate under a nitrogen atmosphere at ambient temperature, then the resulting mixture was adjusted to about pH 8 using sodium hydroxide or hydrochloric acid solution to dissolve the added pemetrexed. A mixed solution of aqueous sodium formate solution and 120 g of ethanol was added, wherein the aqueous sodium formate solution was formed with 140 g of water and 30 g of sodium formate. The resulting mixture was stirred additional 1-2 h at ambient temperature and filtrated. The cake was washed with an appropriate amount of aqueous ethanol and dried to obtain 19.4 g of disodium pemetrexed. The purity of the resulting disodium pemetrexed is 98.6% as measured by HPLC.

EXAMPLEs 5-9 crude wet pemetrexed of different purities was purified according to the above procedure in example 3:

|  | the purity of crude pemetrexed as measured by HPLC | the amount of crude pemetrexed added (based on dry pemetrexed) | the purity of disodium pemetrexed as measured by HPLC after purification | the amount of disodium pemetrexed obtained after purification |
|---|---|---|---|---|
| Example 5 | 59.1% | 10 g | 97.7% | 4.7 g |
| Example 6 | 65.1% | 10 g | 98.0% | 5.8 g |
| Example 7 | 77.7% | 10 g | 98.3% | 7.6 g |
| Example 8 | 89.4% | 10 g | 98.8% | 9.2 g |
| Example 9 | 90.1% | 10 g | 99.1% | 38.7 g |

EXAMPLEs 10-15

Crude disodium pemetrexed or pemetrexed was purified using different water-soluble sodium salts according to the above procedure in example 1 or 3:

|  | the name of crude products | the purity of crude products as measured by HPLC | water-soluble sodium salts | the amount of products after purification |
|---|---|---|---|---|
| Example 10 | Crude disodium pemetrexed | 97.2% | sodium bromide | 99.5% |
| Example 11 | Crude disodium pemetrexed | 98.0% | sodium iodide | 99.8% |
| Example 12 | Crude disodium pemetrexed | 96.8% | sodium sulfate | 99.6% |
| Example 13 | Crude pemetrexed | 88.3% | sodium chloride | 98.4% |
| Example 14 | Crude pemetrexed | 89.7% | sodium acetate | 99.1% |
| Example 15 | Crude pemetrexed | 85.6% | sodium methanesulfonate | 98.5% |

EXAMPLE 16

Purification of Potassium Pemetrexed 15 g of crude, wet pemetrexed (the purity is 85.4%, as measured by HPLC) (corresponding to about 5 g of dry pemetrexed) was added to 40 g of water under a nitrogen atmosphere at ambient temperature, then the resulting mixture was adjusted to about pH11-12 using potassium hydroxide solution to obtain a clear solution. 20 g of saturated potassium chloride aqueous solution was added with stirring, then the resulting mixture was adjusted to pH 8 using hydrochloric acid solution. The mixture was stirred additional 1-2 h at ambient temperature and filtrated. The cake was washed with an appropriate amount of aqueous ethanol and dried to obtain 4.9 g of potassium pemetrexed. The purity of the resulting potassium pemetrexed is 98.5% as measured by HPLC.

EXAMPLE 17

Purification of Potassium Pemetrexed 30 g of crude, wet pemetrexed (the purity is 85.4%, as measured by HPLC) (corresponding to about 10 g of dry pemetrexed) was added to an aqueous potassium formate solution formed with 30 g of water and 4 g of potassium formate under a nitrogen atmosphere at ambient temperature, then the resulting mixture was adjusted to about pH 8 using potassium hydroxide or hydrochloric acid solution to dissolve the added pemetrexed. An aqueous potassium formate solution formed with 60 g of water and 10 g of potassium formate was added with stirring. The resulting mixture was stirred additional 1-2 h at ambient temperature and filtrated. The cake was washed with an appropriate amount of aqueous ethanol and dried to obtain 9.7 g of potassium pemetrexed. The purity of the resulting potassium pemetrexed is 98.1% as measured by HPLC.

EXAMPLE 18

Purification of Lithium Pemetrexed 30 g of crude, wet pemetrexed (the purity is 85.4%, as measured by HPLC) (corresponding to about 10 g of dry pemetrexed) was added to 80 g of water at ambient temperature, then the resulting mixture was adjusted to about pH 11-12 using potassium hydroxide solution to obtain a clear solution. 60 g of half saturated lithium bromide solution was added with stirring, then the resulting mixture was adjusted to pH 8 using lithium hydroxide or hydrochloric acid solution. The mixture was stirred additional 1-2 h at ambient temperature and filtrated. The cake was washed with an appropriate amount of aqueous ethanol and dried to obtain 8.4 g of lithium pemetrexed. The purity of the resulting lithium pemetrexed is 97.3% as measured by HPLC.

The above description is only the preferred modes to carrying out the present invention. It should be noted that one skilled in the art could make modifications or variations without departing from the principle of the present invention. These modifications or variations are regarded to be included within the scope of the following claims.

What is claimed is:

1. A method of purifying a salt of pemetrexed having a structure of formula (III),

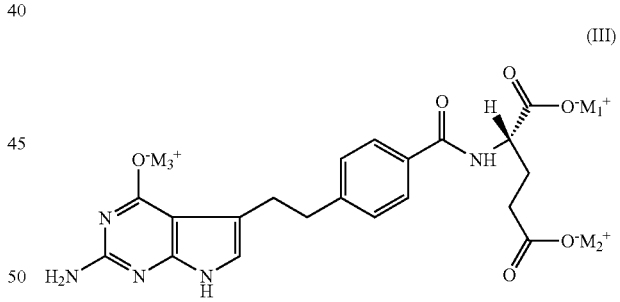

by salting-out of the salt of pemetrexed, wherein,
if $M_3^+$ is $H^+$, then each of $M_1^+$ and $M_2^+$ is independently $H^+$, $Li^+$, $Na^+$ or $K^+$, provided that both of $M_1^+$ and $M_2^+$ are not $H^+$; and
if $M_3^+$ is $Li^+$, $Na^+$ or $K^+$, then each of $M_1^+$ and $M_2^+$ is independently $Li^+$, $Na^+$ or $K^+$;
wherein the salting-out of the salt of pemetrexed comprises:
a) adding an amount of one or more other water-soluble salts and optionally one or more water-miscible organic solvents to supersaturate the salt of pemetrexed in an aqueous solution, wherein the total molarity of the water-soluble salts is between 20% of the saturation concentration thereof and the saturation concentration thereof;

b) adjusting the pH of the solution to a value of at least 5 to crystallize the salt of pemetrexed, wherein the adjusting of pH is unnecessary if the pH is already within this range; and
c) crystallizing sufficiently and then separating the resultant solid by filtration or centrifugation;
to obtain the salt of pemetrexed.

2. A method of purifying a sodium salt of pemetrexed having a structure of formula (III),

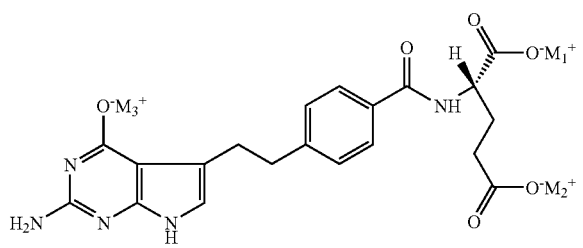

by salting the sodium salt of pemetrexed out from an aqueous solution containing the sodium salt of pemetrexed, one or more other water-soluble salts and optionally one or more water-miscible organic solvents; wherein if $M_3^+$ is $H^+$, then each of $M_1^+$ and $M_2^+$ is independently $H^+$ or $Na^+$, provided that both of $M_1^+$ and $M_2^+$ are not $H^+$; or each of $M_1^+$, $M_2^+$ and $M_3^+$ is $Na^+$, the method comprising a) adding an amount of one or more other water-soluble sodium salts and optionally one or more water-miscible organic solvents to supersaturate the sodium salt of pemetrexed in the aqueous solution, wherein the total molarity of the water-soluble salts is between 20% of the saturation concentration thereof and the saturation concentration thereof;
b) adjusting the pH of the solution to a value of at least 5 to crystallize the sodium salt of pemetrexed, wherein the adjusting of pH is unnecessary if the pH is already within this range; and
c) crystallizing sufficiently and then separating the resultant solid by filtration or centrifugation;
to obtain the sodium salt of pemetrexed.

3. A method of purifying a disodium salt of pemetrexed having a structure of formula (III),

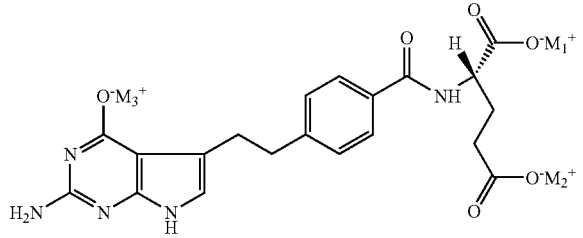

by salting the disodium salt of pemetrexed out from an aqueous solution containing the disodium salt of pemetrexed, one or more other water-soluble sodium salts and optionally one or more water-miscible organic solvents; wherein $M_3^+$ is $H^+$, and each of $M_1^+$ and $M_2^+$ is $Na^+$, the method comprising:

a) adding an amount of one or more other water-soluble sodium salts and optionally one or more water-miscible organic solvents to supersaturate the disodium salt of pemetrexed in the aqueous solution, wherein the total molarity of the water-soluble salts is between 20% of the saturation concentration thereof and the saturation concentration thereof;
b) adjusting the pH of the solution to a value of 6-12 to crystallize the disodium salt of pemetrexed, wherein the adjusting of pH is unnecessary if the pH is already within this range; and
c) crystallizing sufficiently and then separating the resultant solid by filtration or centrifugation;
to obtain the disodium salt of pemetrexed.

4. The purification method according to any one of claims 2 and 3, wherein the one or more other water-soluble sodium salts are selected from the group consisting of sodium fluoride, sodium chloride, sodium bromide, sodium iodide, sodium hydroxide, sodium sulfide, sodium carbonate, sodium bicarbonate, sodium nitrate, sodium nitrite, sodium phosphate, sodium dihydrogen phosphate, disodium hydrogen phosphate, sodium dihydrogen phosphite, disodium hydrogen phosphite, sodium hypophosphite, sodium pyrophosphate, sodium hydrogen pyrophosphate, sodium sulfate, sodium sulfite, sodium hyposulfite, sodium pyrosulfate, sodium pyrosulfite, sodium bisulfite, sodium thiosulphate, sodium borate, sodium molyadate, sodium formate, sodium acetate, sodium propionate, sodium isovalerate, sodium oxalate, sodium citrate, sodium glutamate, sodium tartrate, disodium edetate, sodium benzoate, sodium benzenedicarboxylate, sodium methanesulfonate, sodium methanesulfonate dihydrate, sodium ethanesulfonate, sodium benzenesulfonate, sodium p-toluenesulfonate, sodium phenolate, and a mixture thereof.

5. The purification method according to claim 3, wherein the pH in step b) is adjusted to a value of 7-9 to crystallize the disodium salt of pemetrexed, wherein the adjusting of pH is unnecessary if the pH is already within this range.

* * * * *